(12) United States Patent
Khaligh-Razavi et al.

(10) Patent No.: US 10,010,284 B2
(45) Date of Patent: Jul. 3, 2018

(54) SYSTEM FOR ASSESSING A MENTAL HEALTH DISORDER

(71) Applicant: COGNETIVITY LTD., Camden, London (GB)

(72) Inventors: Seyed-Mahdi Khaligh-Razavi, London (GB); Sina Habibi, London (GB)

(73) Assignee: COGNETIVITY LTD., London (GB)

( * ) Notice: Subject to any disclaimer, the term of this patent is extended or adjusted under 35 U.S.C. 154(b) by 251 days.

(21) Appl. No.: 15/034,597

(22) PCT Filed: Nov. 5, 2014

(86) PCT No.: PCT/GB2014/053298
§ 371 (c)(1),
(2) Date: May 5, 2016

(87) PCT Pub. No.: WO2015/067945
PCT Pub. Date: May 14, 2015

(65) Prior Publication Data
US 2016/0278682 A1    Sep. 29, 2016

(30) Foreign Application Priority Data
Nov. 6, 2013  (GB) .................................. 1319619.1

(51) Int. Cl.
*A61B 5/16*      (2006.01)
*A61B 5/00*      (2006.01)
*G06F 19/00*    (2018.01)

(52) U.S. Cl.
CPC .............. *A61B 5/162* (2013.01); *A61B 5/161* (2013.01); *A61B 5/40* (2013.01); *A61B 5/4076* (2013.01);
(Continued)

(58) Field of Classification Search
CPC ........... A61B 5/161; A61B 5/162; A61B 5/40; A61B 5/4076; A61B 5/4082; A61B 5/4088; A61B 5/742; A61B 5/7264
See application file for complete search history.

(56) References Cited

U.S. PATENT DOCUMENTS

| 8,777,630 B2 * | 7/2014 | Duffy | A61B 5/16 434/167 |
| 8,974,231 B2 * | 3/2015 | Duffy | A61B 5/16 434/167 |

(Continued)

FOREIGN PATENT DOCUMENTS

| JP | 2002/140429 A | 5/2002 |
| WO | 2004/027734 A1 | 4/2004 |

OTHER PUBLICATIONS

Armstrong, R. "The visual cortex in Alzheimer disease: laminar distribution of the pathological changes in visual areas V1 and V2." (2012): 99-128.

(Continued)

*Primary Examiner* — William H McCulloch, Jr.
(74) *Attorney, Agent, or Firm* — Meunier Carlin & Curfman LLC (57) ABSTRACT

A system for assessing a mental health disorder in a human subject, the system comprising: a display configured to display a series of natural test images to the subject; an input by which the subject can input a response, following the display of each test image, as to whether or not the test image satisfies a predetermined categorization criterion; a control processor configured to control the display of the test images by the display, to measure the duration of time from when each test image is initially displayed to when the corresponding response is input by the subject, and to generate a set of response data including the response times in respect of each of the test images; and a data processor (Continued)

configured to process the set of response data and to compare the processed response data with reference data to assess whether or not the subject has, or is likely to develop, the mental health disorder.

19 Claims, 7 Drawing Sheets

(52) U.S. Cl.
CPC .......... *A61B 5/4082* (2013.01); *A61B 5/4088* (2013.01); *A61B 5/7257* (2013.01); *A61B 5/7264* (2013.01); *A61B 5/742* (2013.01); *G06F 19/345* (2013.01); *G06F 19/363* (2013.01); *A61B 5/0022* (2013.01); *A61B 5/7246* (2013.01); *A61B 5/7267* (2013.01); *A61B 5/7275* (2013.01)

(56) References Cited

U.S. PATENT DOCUMENTS

| | | | | |
|---|---|---|---|---|
| 8,979,547 | B2* | 3/2015 | Duffy | A61B 5/16 434/167 |
| 9,095,295 | B2* | 8/2015 | Eagleman | A61B 5/161 |
| 9,861,307 | B2* | 1/2018 | Klin | A61B 5/165 |
| 2002/0143240 | A1* | 10/2002 | Teicher | A61B 5/1118 600/300 |
| 2003/0073885 | A1* | 4/2003 | Theodoracopulos | A61B 5/16 600/300 |
| 2003/0233032 | A1* | 12/2003 | Teicher | A61B 5/1118 600/300 |
| 2005/0273017 | A1* | 12/2005 | Gordon | A61B 5/048 600/544 |
| 2006/0074340 | A1* | 4/2006 | Murata | A61B 5/16 600/558 |
| 2007/0166675 | A1* | 7/2007 | Atkins | G09B 5/06 434/236 |
| 2009/0270758 | A1* | 10/2009 | Eagleman | A61B 5/161 600/558 |
| 2011/0065075 | A1* | 3/2011 | Duffy | A61B 5/16 434/236 |
| 2012/0022395 | A1* | 1/2012 | Kinkingnehun | A61B 3/145 600/558 |
| 2014/0370479 | A1* | 12/2014 | Gazzaley | A61B 5/162 434/322 |
| 2016/0125748 | A1* | 5/2016 | Ashford | G09B 5/00 434/236 |
| 2016/0278682 | A1* | 9/2016 | Khaligh-Razavi | A61B 5/7264 |
| 2018/0021579 | A1* | 1/2018 | Kahana | A61N 1/36082 |

OTHER PUBLICATIONS

Brewer, A.A., et al. "Visual cortex in aging and Alzheimer's disease: changes in visual field maps and population receptive fields." Frontiers in psychology 5 (2014).

Chandler, D.M., et al. "Estimates of the information content and dimensionality of natural scenes from proximity distributions." JOSA A 24.4 (2007): 922-941.

Gordon, B., et al. "The basis for choice reaction time slowing in Alzheimer's disease." Brain and cognition 13.2 (1990): 148-166.

Jahanshahi, M., et al. "Simple and choice reaction time and the use of advance information for motor preparation in Parkinson's disease." Brain 115.2 (1992): 539-564.

Knopman, D., et al. "Procedural learning is impaired in Huntington's disease: Evidence from the serial reaction time task." Neuropsychologia 29.3 (1991): 245-254.

Mentis, M.J., et al. "Visual cortical dysfunction in Alzheimer's disease evaluated with a temporally graded 'stress test' during PET." Am J Psychiatry 153 (1996): 32-40.

Mirzaei, A., et al. "Predicting the human reaction time based on natural image statistics in a rapid categorization task." Vision research 81 (2013): 36-44.

Rinehart, N.J., et al. "Movement preparation in high-functioning autism and Asperger disorder: a serial choice reaction time task involving motor reprogramming." Journal of autism and developmental disorders 31.1 (2001): 79-88.

NeuroTrax Corporation, "Mindstreams computerized cognitive tests," XP002972976, Jan. 1, 2003, 14 pages.

International Search Report and Written Opinion of the International Searching Authority for application No. PCT/GB2014/053298, dated Jan. 23, 2015, 12 pages.

International Preliminary Report on Patentability issued by the International Preliminary Examining Authority for application No. PCT/GB2014/053298, dated Feb. 25, 2016, 18 pages.

* cited by examiner

SYSTEM FOR ASSESSING A MENTAL HEALTH DISORDER

FIELD OF THE INVENTION

The present invention relates to a system for assessing a mental health disorder. It is particularly applicable, but by no means limited, to the diagnosis of dementia—in particular (but not exclusively) Alzheimer's disease.

BACKGROUND TO THE INVENTION

Mental health disorders affect many people around the world. Among such disorders, dementia is particularly common among the elderly. According to recent statistics, 800,000 people in the UK alone (according to the Alzheimer's Society) and 36 million worldwide (according to the World Health Organisation) currently have dementia, with the numbers doubling every 20 years. One in three people over the age of 65 will end their lives with dementia. 46% of people with dementia living in the UK never receive a diagnosis. National Health Service memory clinic waiting lists in the UK average six months (up to 18 months), and undergoing the full diagnostic process within the clinic usually takes another six months. Thus, to alleviate the burden and reduce the waiting lists for such clinics, there is a desire to be able to diagnose dementia quickly and easily.

Furthermore, brain changes underlying Alzheimer's disease develop over a period of at least 20-30 years prior to the onset of symptoms. The diagnosis is often not made at all, or made very late in the process, by which time cognitive impairment, disability and behavioural symptoms may be all quite marked. There is therefore a desire to advance the time at which diagnosis can be made. Through doing so, it is hoped that future treatments could then target the disease in its earliest stages, before irreversible brain damage or mental decline has occurred.

Moreover, the impact of a dementia diagnosis depends greatly upon how it is made and imparted. Evidence suggests that when people with dementia and their families are well prepared and supported, initial feelings of shock, anger and grief are balanced by a sense of reassurance and empowerment. Thus, early diagnosis of dementia is desirable, to allow people with dementia to plan ahead while they still have the capacity to make important decisions about their future care. In addition, they and their families will be able to receive timely practical information, advice and support. Only through receiving a diagnosis are they able to get access to available drug and non-drug therapies that may improve their cognition and enhance their quality of life. And they can, if they choose, participate in research for the benefit of future generations.

In the UK the lead specialty that has evolved to diagnose and treat people with dementia is old age psychiatry. However, diagnosis and treatment might also be carried out by a geriatrician (e.g. if there is concomitant acute physical illness requiring admission to a general hospital), a neurologist, adult psychiatrist, liaison psychiatrist, neuropsychiatrist (e.g. where the person is relatively young) or a GP (where the GP has a particular skill or interest in the area). Although families provide the majority of care received by people with dementia, professional health care can be vital to the individual with dementia and their family. A lack of diagnosis means a lack of specific treatment and care for dementia. Diagnosis is the gateway for care.

Dementia is conventionally diagnosed when progressive cognitive decline has occurred, and this has had a noticeable impact upon a person's ability to carry out important everyday activities. It is a clinical diagnosis, supported by careful neuropsychological testing, a history from the patient (subjective impairment in memory and other cognitive functions) and from a key informant (objective signs suggestive of cognitive decline, and evidence of impact on social and/or occupational functioning). Neuroimaging is used, where available, to exclude other organic causes of cognitive impairment, and to provide information supporting definition of subtype. Other tests may be done to rule out other causes of cognitive changes such as thyroid disease, vitamin deficiencies or infection.

However, even with advanced existing techniques, dementia diagnosis rates are very low. Of the 800,000 people living with dementia in the UK, less than half have received diagnosis. Without diagnosis patients are denied access to support, information and potential treatments that can help them to live well, and as their condition develops it is likely to become more costly for the health service to treat. It is also shown that the rate of diagnosis varies dramatically from one geographical location to another (35% in Southwest England, to over 70% in parts of Scotland and Northern Ireland). This further highlights the inefficiencies in the existing diagnosis process.

Likewise, in the US, dementia is the sixth most common cause of death, costing the economy US$216 billion in 2012. By 2019, more than 100 million Americans will be over age 50. Roughly 1 in 8 will develop dementia over age 65 (Alzheimer's Association 2012). Despite the common myth that nothing can be done for affected patients, it is now proven that the disease symptoms can be delayed for years if the medication is started prior to the progressive phase. Also, latest studies show that the disease possibly could be cured if diagnosed at an early stage of development known as mild cognitive impairment (MCI).

More than five million Americans currently have Alzheimer's disease. By 2050, nearly 14 million (13.8 million) Americans could be living with the disease, unless scientists develop new approaches to prevent or cure it.

Worldwide, nearly 36 million people are believed to be living with Alzheimer's disease or other dementias. By 2030, if breakthroughs are not discovered, we will see an increase to nearly 66 million. By 2050, rates could exceed 115 million.

Total payments for health care, long-term care, and hospice care for people with Alzheimer's disease and other dementias are projected to increase from US$200 billion in 2012 to US$1.1 trillion in 2050 (in 2012 dollars). This dramatic rise includes a six-fold increase in government spending and a five-fold increase in out-of-pocket spending.

People who have Alzheimer's disease need others to care for them, and many of those providing care are not paid for their time and services. For example, more than 15 million Americans provide unpaid care for someone with Alzheimer's disease or dementia. Unpaid caregivers are usually immediate family members or other relatives and friends. In 2011, these people provided an estimated 17.4 billion hours of unpaid care, a contribution valued at more than US$210 billion.

The bulk of the publications in this field focus on memory tests. Some attempts have been made to look at response times. For example, WO02078536A1 looks at response time tests on visual images for AD and other conditions. US2002072859A1 relates to a test for the onset of dementia using visual images. It also mentions fatigue. WO2004060164A1 discloses a test including a test stimulus, masking, user response; perception of characteristic and response time. Data is first built up on a user through repetition and then a determination of cognitive impairment is made.

Thus, in view of the above issues, the present work seeks to provide a way of obtaining early detection of dementia. Surprisingly, we have found that the use of natural images allows for early detection of dementia, prior to onset of memory-loss symptoms.

SUMMARY OF THE INVENTION

According to a first aspect of the invention there is provided a system for assessing a mental health disorder in a human subject, the system comprising: a display configured to display a series of natural test images to the subject; an input by which the subject can input a response, following the display of each test image, as to whether or not the test image satisfies a predetermined categorisation criterion; a control processor configured to control the display of the test images by the display, to measure the duration of time from when each test image is initially displayed to when the corresponding response is input by the subject, and to generate a set of response data including the response times in respect of each of the test images; and a data processor configured to process the set of response data and to compare the processed response data with reference data to assess whether or not the subject has, or is likely to develop, the mental health disorder.

The terms "natural image" or "natural test image" as used herein refer to images (e.g. photographs) or drawings of natural scenes such as animals, as opposed to purely abstract or man-made drawings or images such as straight lines or dots.

Preferably, the system is configured to display a mask (masking image). In presently-preferred embodiments, the control processor are configured to cause the display to display one or more mask images after each test image. For example, the control processor may be configured to cause the display to display a blank screen followed by a noisy mask after each test image.

In presently-preferred embodiments the method provides a rapid categorisation task to the subject, i.e. it requires the subject to respond rapidly with its categorisation response (category selection, being the subject's response as to whether or not the test image satisfies the predetermined categorisation criterion).

In presently-preferred embodiments control processor is configured to cause the display to display each test image for a duration of the order of 10 ms, followed by a blank screen for a duration of the order of 10 ms, followed by a noisy mask for a duration of the order of 100 ms or longer.

In one such embodiment, the control processor are configured to cause the display to display each test image for 12.5 ms, followed by a blank screen for a variable length of time, followed by a noisy mask. The blank screen is preferably displayed for a variable length of time of between 11.9 ms and 13.1 ms (i.e. 12.5±0.6 ms) after each test image. However, in alternative embodiments different lengths of time may be used instead.

In presently-preferred embodiments the control processor are configured to cause the display to display 1/f or 'pink' noise as the noisy mask. However, in other embodiments other types of noise or masking effects may be used after each test image.

In presently-preferred embodiments the predetermined categorisation criterion is whether the image includes an animal. This has been found to be particularly effective as a criterion to test the subject's mental processing ability, as well as their motor skills when providing a response, engaging a large volume of cortex including areas affected in the early stages of a mental health disorder.

Preferably the control processor are configured to cause the display to display a total of approximately 500 test images to the subject during the course of a test.

In certain embodiments the data processor may be configured to compare the processed response data with reference data obtained by previously testing subjects without the mental health disorder and subjects with the mental health disorder.

Alternatively, or in addition, the data processor may be configured to compare the processed response data with predicted or estimated reference data obtained by performing statistical analysis on one or more of the test images used. This enables the present process to be extended to use natural images which have not previously been used on known "healthy" or "non-healthy" subjects.

Statistical analysis may be used to obtain a measure of the complexity of such an image, which can be used to derive predicted or estimated reaction times for that image. In presently-preferred embodiments the statistical analysis takes into account one or more of the entropy, Weibull distribution and/or Fourier analysis of the test images.

In presently-preferred embodiments the data processor are configured to process the set of response data so as to produce a vector of reaction times in respect of the subject, and to compare said vector with clusters of such vectors representative of healthy and non-healthy subjects. The present method may include an initial data collection ("training") phase, including the collection and analysis of "training" data using known healthy or non-healthy subjects. In presently-preferred embodiments, for known healthy subjects, the response reaction time data is used to create a cluster of results. Different clusters of results are preferably seen for healthy and non-healthy subjects. A linear regression model may also be fitted between reaction times and each of the image statistics.

Following the optional and initial data collection or "training" phase described above, it is preferred that the method includes measurement of individual candidate subjects' response reaction times. Based on the patterns of reaction times, the method preferably discriminates healthy vs. non-healthy subjects (i.e. those with or without dementia, including AD, including early onset discrimination).

In presently-preferred embodiments, the method may also include machine learning. For example, after obtaining data from a new candidate subject, this data may be added to the applicable cluster of healthy or non-healthy subjects obtained from the "training" phase. This enables the method to progressively grow the body of data against which future candidate subjects can be assessed.

Also provided is a database of patient information. The database is preferably anonymised, for example in order to comply with local regulations. The database may be as described herein. It may typically include response times and information on whether the patient was healthy or not.

In presently-preferred embodiments, natural image statistics may predict reaction times to new images.

In presently-preferred embodiments, natural image statistics may be used to construct patterns of correlations (clusters) between reaction times and image statistics. These patterns may then be used for categorizing participants as healthy or unhealthy.

In presently-preferred embodiments, natural image statistics may predict reaction times to new images. These may be used to construct patterns of correlations (clusters) between reaction times and image statistics. As above, these patterns may then be used for categorizing participants as healthy or unhealthy.

The control processor and the data processor may be provided within a single processing device (e.g. a personal computer). Alternatively the control processor may be provided within a first processing device (e.g. a terminal computer), and the data processor may be provided within a second processing device (e.g. a remote server). In such a case, the remote server may be configured to send details of its assessment to the terminal computer.

The system may further comprise a data storage device in communication with the data processor, for storing the results produced.

The data processor may be configured to add to the reference data the response data obtained in respect of the subject, once the mental health of the subject has been diagnosed.

In certain embodiments the data storage device may be configured to store multiple instances of results obtained over time from a given subject. In such a manner, the system can perform trend analysis on the results obtained from the given subject over time, for example to detect the onset of the mental health disorder.

In certain embodiments the mental health disorder is dementia—in particular, Alzheimer's disease. However, in alternative embodiments other mental health disorders may be detected. Further examples are provided herein.

The method is preferably performed at one sitting or in a unitary manner. This is distinct from where elements of the test are used separately and without correlation between them.

According to a second aspect of the invention there is provided a computerised method for assessing a mental health disorder in a human subject, the method comprising: displaying a series of natural test images to the subject; receiving response input from the subject, following the display of each test image, as to whether or not the test image satisfies a predetermined categorisation criterion; measuring the duration of time from when each test image is initially displayed to when the corresponding response input is received from the subject; generating a set of response data including the response times in respect of each of the test images; and processing the set of response data and comparing the processed response data with reference data to assess whether or not the subject has, or is likely to develop, the mental health disorder.

According to a third aspect of the invention, there is provided a method of treating a mental health disorder in a subject, comprising assessing a subject as desired herein and treating the subject as appropriate. For example, for a subject determined to be at risk of or having dementia or early stage dementia, the treatment may be to administer drugs, such as acetylcholinesterase inhibitors, or undergo non-drug treatment such as cognitive enhancement therapy.

Preferable or optional features in relation to the second and third aspects of the invention correspond to those set out above in relation to the first aspect of the invention.

According to a fourth aspect of the invention, there is provided a computer program or set of instruction code which, when executed by processor, causes the processor to function as the processor of the first aspect of the invention, and/or to implement the method of the second aspect of the invention.

According to a fifth aspect of the invention there is provided a computer-readable medium or physical carrier signal encoding a computer program or set of instruction code in accordance with the third aspect of the invention.

According to a sixth aspect, the invention provides a device for assessing a subject in accordance with the invention. The device may as described herein. It may be a tablet or smartphone. The device will typically comprise a display configured to display a series of natural test images to the subject; an input by which the subject can input a response, following the display of each test image, as to whether or not the test image satisfies a predetermined categorisation criterion; and a control processor configured to control the display of the test images by the display.

The device may communicate with a server to measure the duration of time from when each test image is initially displayed to when the corresponding response is input by the subject, and to generate a set of response data including the response times in respect of each of the test images. Alternatively, the device may measure this itself and communicate with a server which generates a set of response data including the response times in respect of each of the test images. Optionally, the generation of a set of response data may occur on the device itself.

Similarly, the data processor (configured to process the set of response data and to compare the processed response data with reference data to assess whether or not the subject has, or is likely to develop, the mental health disorder) may be on a separate server or on the device itself.

According to a further aspect of the invention there is provided a system for assessing a mental health disorder in a human subject, the system comprising: display means configured to display a series of natural test images to the subject; input means by which the subject can input a response, following the display of each test image, as to whether or not the test image satisfies a predetermined categorisation criterion; control processing means configured to control the display of the test images by the display means, to measure the duration of time from when each test image is initially displayed to when the corresponding response is input by the subject, and to generate a set of response data including the response times in respect of each of the test images; and data processing means configured to process the set of response data and to compare the processed response data with reference data to assess whether or not the subject has, or is likely to develop, the mental health disorder.

Also provided is a system for assessing a mental health disorder substantially as herein described with reference to and as illustrated in any combination of the accompanying drawings; a computerised method for assessing a mental health disorder substantially as herein described with reference to and as illustrated in any combination of the accompanying drawings; or a computer program or set of instruction code substantially as herein described with reference to and as illustrated in any combination of the accompanying drawings.

BRIEF DESCRIPTION OF THE DRAWINGS

Embodiments of the invention will now be described, by way of example only, and with reference to the drawings in which.

DETAILED DESCRIPTION OF PREFERRED EMBODIMENTS

The present embodiments represent the best ways known to the applicants of putting the invention into practice. However, they are not the only ways in which this can be achieved.

The method of the invention can be used to diagnose and distinguish various forms of dementia, including dementia associated with Alzheimer's disease, Lewy body dementia, vascular dementia, frontotemporal degenerative dementias (e. g., Pick's disease, corticobasal ganglionic degenerations, and frontotemporal dementia), Huntington's disease, Creutzfeldt Jakob disease, Parkinson's disease, cerebrovascular disease, head trauma, and substance abuse). Parkinson's' or Huntington's disease are preferred in some embodiments. AD is particularly preferred in some embodiments.

Overview

Earlier studies have suggested that response reaction time is usually affected by different type of brain diseases (Gordon and Carson, 1990; Jahanshahi et al., 1992; Knopman and Nissen, 1991; Rinehart et al., 2001). This suggests that patterns of reaction times can be used for diagnostic purposes.

It has already been shown that reaction time of healthy subjects is correlated with statistical properties of natural images (Mirzaei et al., Vision Research 81, 2013).

We would expect to see different patterns of correlations for healthy subjects vs. those in early stages of the disease.

WO02078536A1 discloses nothing about using natural images such as animals.

In US2002072859A1, there is no mention of natural images, and the stimuli that are used are simple random dots, as opposed to natural images. The subject's task is different from ours. In the present invention, a rapid categorization task is preferred. For example, we display images in the order of only 10 ms in some embodiments. In contrast, however, the task in US2002072859A1 is a visual search to find the target on the display system. This document is also silent on the supplementary benefits of masking.

WO2004060164A1 does mention AD at the very end, but this is an old document in this fast-moving field, published at a time when memory test were popular. Until the present invention, detection of AD through response reaction times has not been experimentally tested alone. Simple response reaction time methods have been used in conjunction with other tests, but not alone as one unified test as we provide. Furthermore, this document does not disclose the use of 'natural test images' nor the use of natural image statistics. The statistical analysis that we use, for example measuring the entropy of a natural image stimulus, is only applicable to natural images, and cannot be applied to simple line drawing images like those used in this publication.

In presently-preferred embodiments of the invention, measuring such entropy (in the test image) is provided. Other statistical analyses of the test image are also preferred.

Vision Research 81 (2013) does disclose the use of 'natural test images,' but only in respect of response times in general. This was the first paper to look at natural images, but there is nothing on how this might be applied in a medical setting, let alone any mention of a disease state, including dementia or AD. The teaching of this document cannot be applied to the art in respect of dementia or AD because the image statistics applied in this paper can only be used on natural images and not on the line-drawing images or random dots used in the dementia art.

We have two preferred and separate applications of natural image statistics:

1) one that is to predict reaction times to new images; and
2) to construct patterns of correlations between reaction times and image statistics, and then to use these patterns for categorizing participants as healthy or unhealthy. Of course, these may also be used in combination.

The first point was used in a non-medical treatment context in the Vision Research 81 (2013) paper. However, the second point was not used or mentioned in that paper at all. The regression methods and the machine learning methods (including the clusterings) used in this second point are very different from the analysis in that paper.

As such, the use of natural images has merit because we have shown that they can help with early detection of dementia, prior to onset of memory-loss symptoms.

By natural images we mean images (e.g. photographs) or drawings of natural scenes, as opposed to purely abstract drawings or images that our visual system is not very often exposed to. Technically speaking, in the present work, a set of natural images consists of images that have a similar statistical structure to those which the human visual system is adapted to. Examples may also include photos taken from scenes such as a jungle, a street, buildings and so forth. Although some of these may be created by man, these images are distinct from 2-dimensional line drawings that are not type of the scenes or images that the subject will typically observe in its life. It may be said that the eye (really the brain) is "programed" to recognise these images. The images may be described as everyday images.

A preferred example of a categorisation task is to respond "animal" or "non-animal". In other embodiments the animal element here may be replaced by other natural items such as a waterfall to provide a categorisation task which is to respond "waterfall" or "non-waterfall". Equally, the element may be replaced by a tree, a flower, a face. or so forth.

The categorisation task may be a two-forced choice categorization task. In this, the subject is asked to say (indicate) whether a specific object exists (i.e. is recognised) in the image, or not.

In the present work, we have developed a computerised psychophysical rapid categorisation task-based test using natural images. Our designed psychophysical computerised test engages a large volume of cortex, mainly visual cortex that is also known to be affected in early stages of Alzheimer's disease (Armstrong, 2012; Brewer and Barton, 2012; Mentis et al., 1996). With the current work we envisage being able to detect the disease even before the onset of memory-loss symptoms.

During an initial "training" data collection phase, known healthy subjects (i.e. people without Alzheimer's disease, as "control" subjects) and subjects with mild cognitive impairment known to be in the early stages of Alzheimer's disease are asked to do the computerised test, in which they are presented with a diverse set of natural images and asked to categorize each image as soon and as accurately as possible by pressing relevant buttons on a keyboard. (The subjects in the early stages of Alzheimer's disease may be referred to herein as "non-healthy" subjects; this terminology is used merely as a way of differentiating such people from those without Alzheimer's disease, and does not imply any other physical or mental unhealthiness.) The results from this initial data collection phase are analysed to obtain two distinct patterns of response reaction times, for the healthy and non-healthy subjects. Consequently models can be developed based on the healthy and non-healthy subjects' reaction times in the categorization task. Thus, at the end of the process, we have two models—one that can be used to predict the reaction time of healthy subjects, and another that can be used to predict the reaction time of non-healthy subjects.

Based on these predicted reaction times to a set of diverse images, in subsequent tests of candidate individuals, using the same test procedure, we can categorize each individual to the category with which his reaction time is mostly correlated. For example, if his reaction times are more correlated with the patterns of reaction times of healthy subjects, then he will be categorized as healthy. On the other hand, if his reaction times are more correlated with the patterns of reaction times of non-healthy subjects, then he will be categorized as non-healthy (i.e. in the early stages of Alzheimer's disease). In this manner, it is possible to diagnose whether or not an individual is the early stages of Alzheimer's disease. It is important to note that all these comparisons between healthy and non-healthy subjects are done across those within the same age group. For example, a candidate subject with an age between 50 to 60 is compared against healthy and non-healthy subjects in the same age group.

Psychophysical Test Process

We run our psychophysical tests in a dark room, which minimizes the possibility for subject distraction. In each test the subject is seated 0.5 m away from a computer screen (80 Hz monitor refresh rate).

Figure 1:
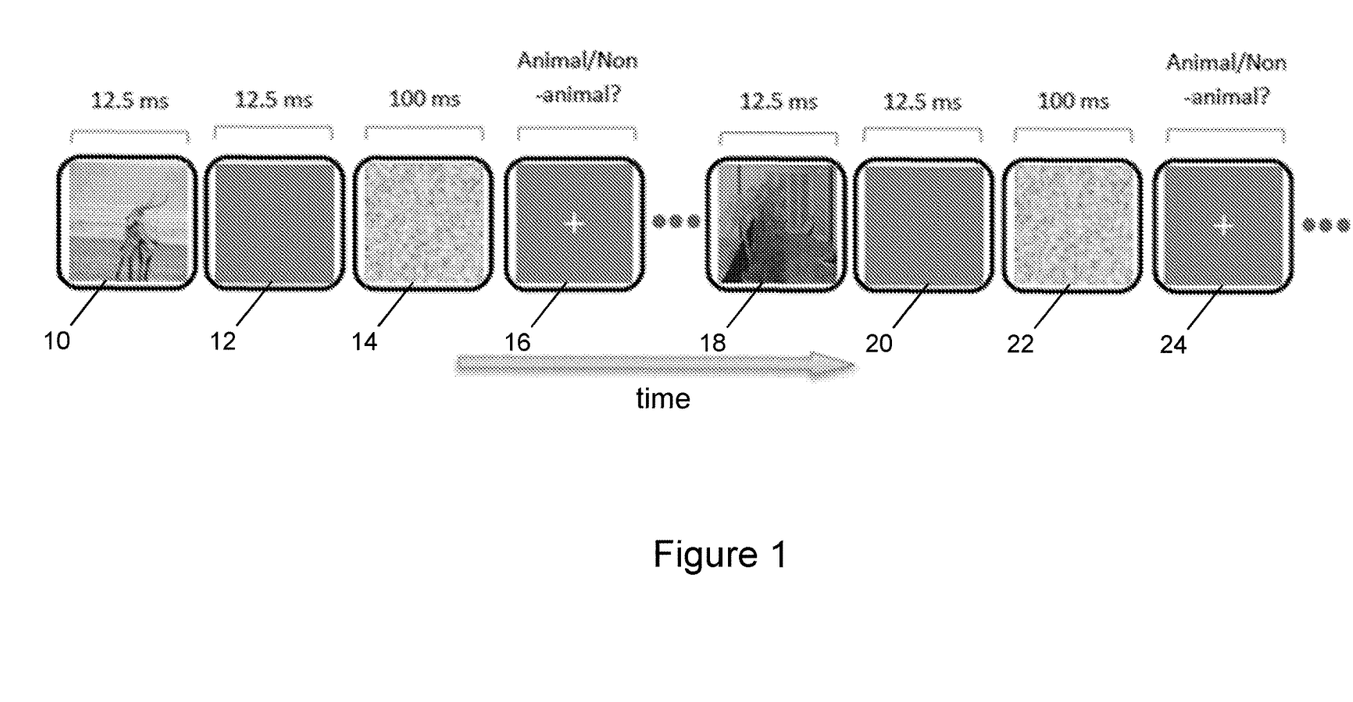
FIG. 1 illustrates an exemplary procedure for a computerised image categorisation task.

As illustrated in FIG. 1, in each test a series of individual greyscale natural images (e.g. 10, 18 etc.) is presented in the centre of the computer screen (~7°×7° of visual angle) to the subject, each image for 12.5 ms. In the presently-preferred embodiments, each natural image 10, 18 includes either an animal or a picture of something other than an animal (i.e. a "non-animal"). Each natural image is followed by a blank screen 12, 20 for 12.5±0.6 ms as an interstimulus interval (ISI). A noisy mask (1/f noise image) 14, 22 of duration 100 ms appears at the end of each ISI. (1/f noise is also known as "pink" noise, which is a signal for which the power spectrum is inversely proportional to the frequency f.) It is important to note that the ISI is randomly varied by approximately ±0.6 ms to avoid adaptation of the subjects. The stimulus onset asynchrony (SOA) is approximately 25 ms (12.5 ms for the image presentation, followed by an ISI of 12.5±0.6 ms).

As a task, the subject is instructed to respond as quickly and accurately as possible, following the display of each natural image, as to whether the presented image satisfies a predetermined categorisation-based criterion. In the presently-preferred embodiments the task is to determine whether each presented image contains an animal or a non-animal (i.e. a so-called "distractor"). In response to each image, the subject is required to press on the computer keyboard either a designated YES key if the image contains an animal, or a designated NO key if the image does not contain an animal. For each image the exact duration of time from when the image first appears to when the subject presses the YES or NO key is recorded as his response reaction time to that image. This is repeated after each image in the series is displayed, with the subject ideally pressing the YES or NO key before the image is replaced by the blank screen. Thus, the present tests are not primarily intended to evaluate the subject's memory as such (i.e. their ability to remember what is shown in the image, before it is blanked out), but rather to assess their ability to mentally process what is shown in the image (i.e. whether or not the image satisfies the predetermined categorisation criterion) and how long it takes them to process the image content. The test process is the same for healthy and non-healthy subjects; in the end for all subjects we have responses to each image (YES or NO) plus the reaction time.

In FIG. 1, screens 16 and 24 indicate a fixation period in which the system waits for the subject's response to each individual trial, before moving on to the next one. Screens 10, 12, 14 and 16 represent an "animal" trial, and screens 18, 20, 22 and 24 represent a "non-animal" trial. In an overall test, animal and non-animal trials are randomly intermixed and there are 500 trials in total.

Figure 2:
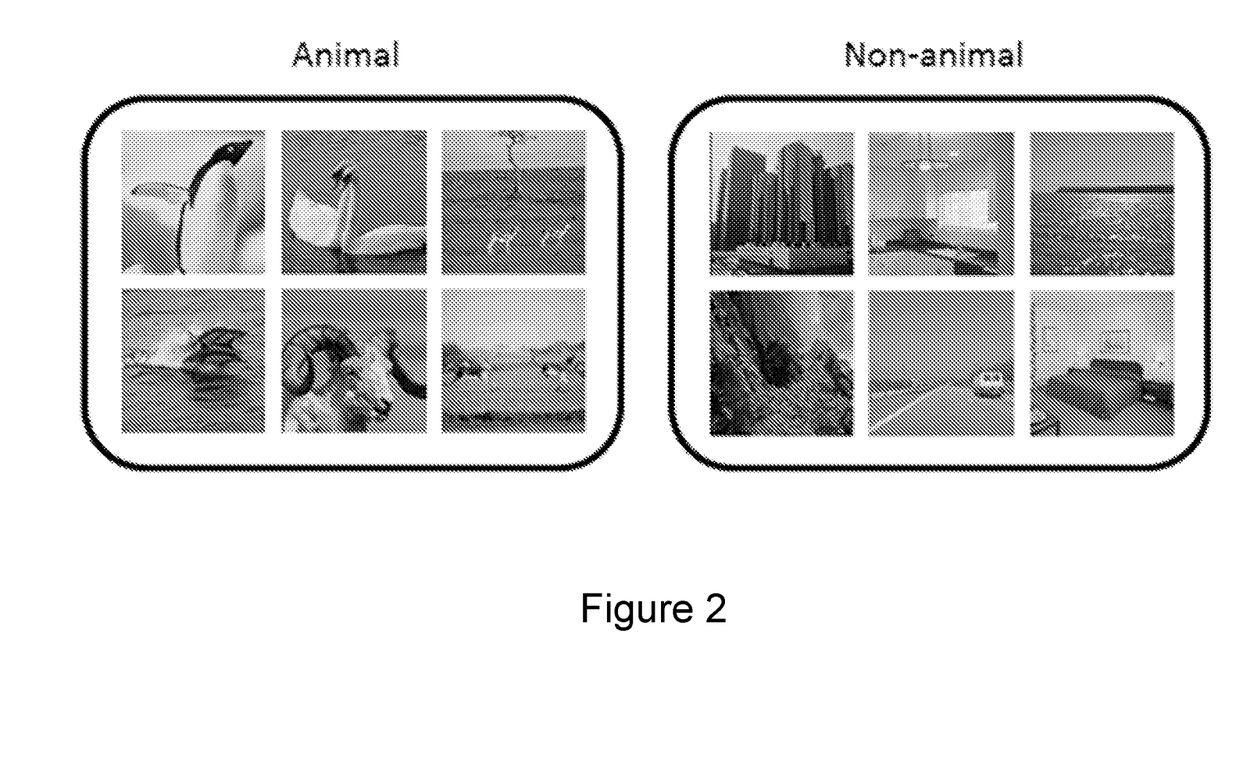
FIG. 2 illustrates examples of "animal" and "non-animal" natural images used in a computerised image categorisation task.

Thus, in each test, many different animal or non-animal images are presented in a manner that is unpredictable to the subject. Examples of typical animal or non-animal images are shown in FIG. 2. It will be appreciated that, with the animal images, the animal may be shown as part of a scene, and other objects may be present (e.g. a tree in the background). Similarly, with the non-animal images, a scene may be shown rather than just a single object. Thus, the subject is required to mentally process the content of each image, to determine whether or not an animal is present, and to respond accordingly.

In a typical test, 500 images are shown to the subject, although this number is not critical and the actual number used may be greater or less than this.

To familiarize each subject with the test process before it begins, each subject is required to perform the same process using different images before participating in the main test. This preparation stage takes approximately 5 minutes per subject.

All subjects should have normal or corrected-to-normal vision and should be unfamiliar with the presented images. The stimulus database consists of 500 natural images, of which 250 contain animals and 250 do not.

Initial Data Collection ("Training") Phase

Figure 3:
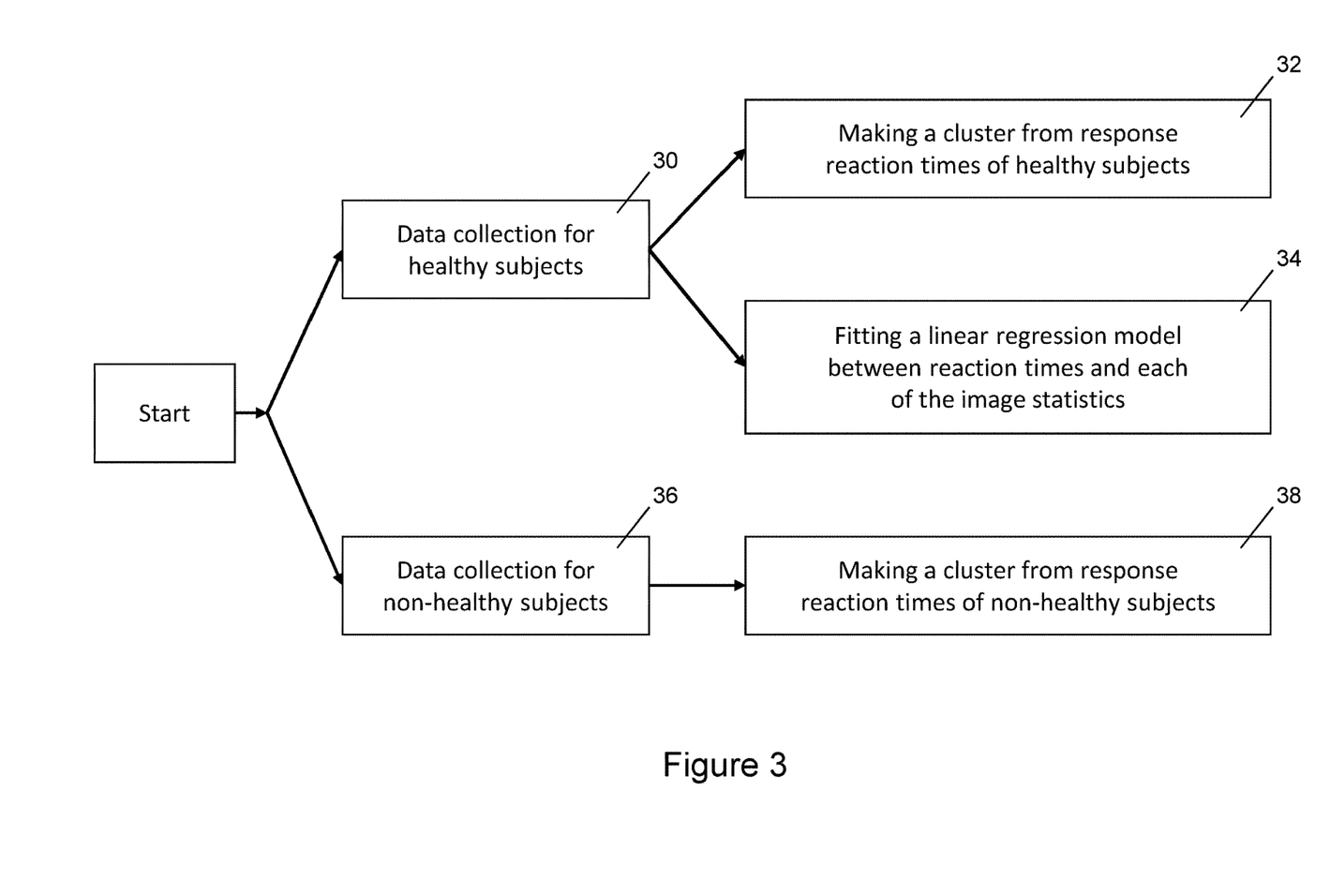
FIG. 3 illustrates an overall procedure for the collection and analysis of training data.

FIG. 3 illustrates in more detail the overall procedure for the collection and analysis of "training" data using known healthy or non-healthy subjects.

Figure 4:
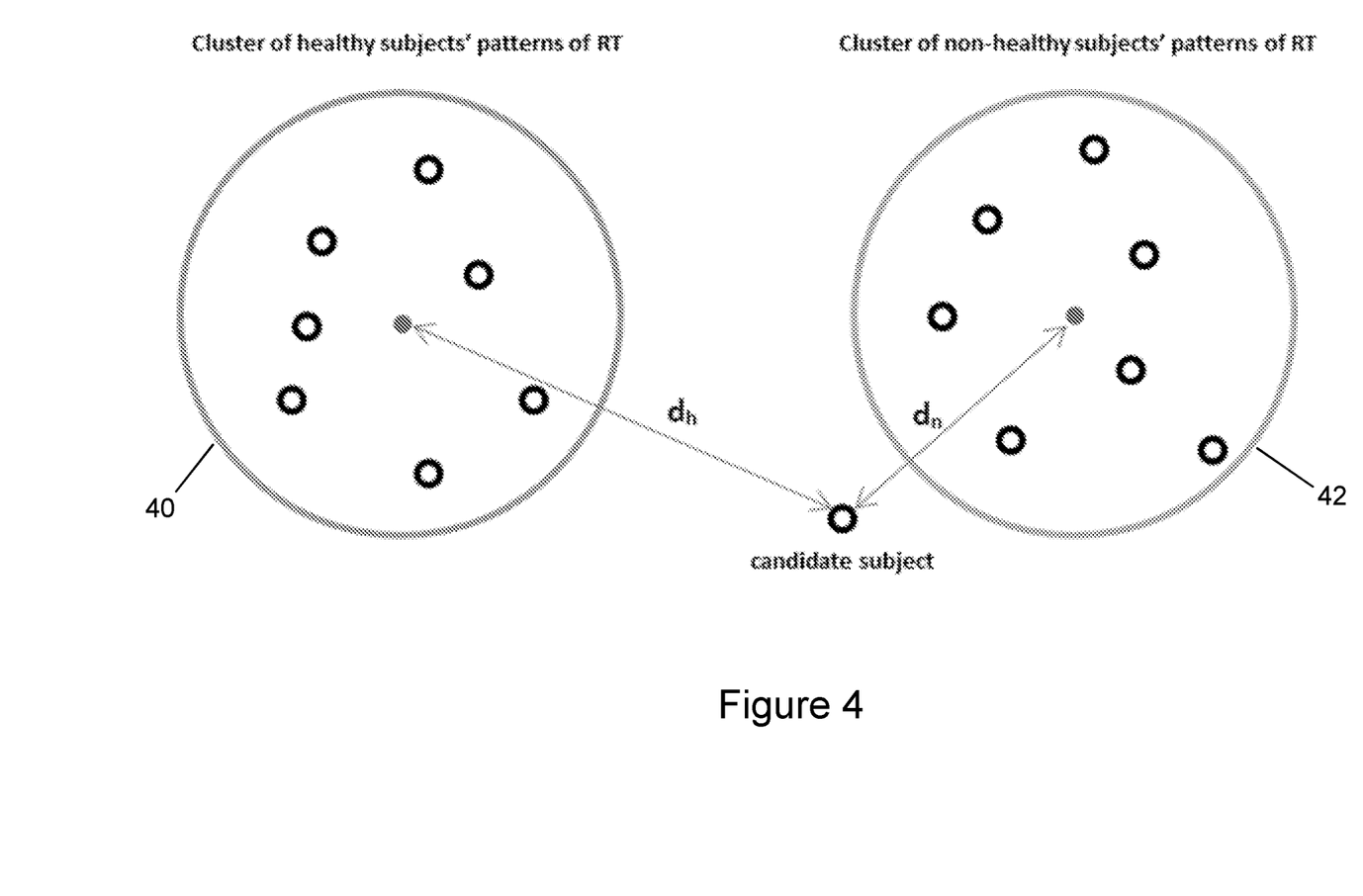
FIG. 4 illustrates the correlation of the results obtained from a candidate subject with the results from the training data.

For known healthy subjects (30), the response reaction time data is used to create a cluster of results (32), such a cluster being illustrated diagrammatically in FIG. 4 (cluster 40). A linear regression model may also be fitted between reaction times and each of the image statistics (34). Examples of the image statistics, and their concatenation into a single vector, will be discussed below. Image statistics for each image are calculated only once.

On the other hand, with non-healthy subjects (36), the response reaction time data is used to create a different cluster of results (38), which is illustrated diagrammatically in FIG. 4 (cluster 42).

Method for Early Diagnosis of Dementia—Testing Candidate Individuals

Following the initial data collection or "training" phase described above, we are able to measure individual candidate subjects' response reaction times to the stimuli in correct trials. Then based on the patterns of reaction times, we are able to discriminate healthy vs. non-healthy subjects (i.e. those with AD). The subject reaction time in the designed task includes the time required for both visual processing and response accomplishment, so a large volume of cortex is engaged, including areas affected in early stages of dementia. As opposed to other cognitive tasks that try to diagnose subjects with AD based on their memory impairments, the designed test targets other brain functionalities rather than memory. The brain changes underlying Alzheimer's disease develop over a period of about 20-30 years prior to the onset of memory-loss symptoms. Thus, with this new cognitive task we aim to diagnose the disease in earlier stages, before the start of memory symptoms.

The process can be extended to other natural images—not used in the training process—by fitting a model to subjects' response reaction times based on statistics of the natural images that are used. Some examples of the statistics that can be used are: gamma and beta of Weibull distribution fitted to the edge histogram of the images; entropy of the images; and Fourier slope and intercept of the images. These image statistics can be used to predict the response reaction time of subjects. By doing so, the response reaction time to new unseen natural images can be predicted for healthy and non-healthy subjects. This generalizes our approach and makes it work with other natural images for which we have not collected subjects' reaction times in the initial "training" phase; instead the reaction times to these images can be predicted using the fitted models. For example, to fit the model for healthy subjects, all image statistics are first calculated for the new set of images. Then using the least square error (LSE) approach, we find the optimal weight vector (w1, w2, w3, w4, w5) that maps the image statistics of the training images to the reaction times obtained in the training phase from healthy subjects (there are five weights, each corresponding to one of the image statistics). Finally, using the best estimated weight vector, the reaction times for healthy subjects are predicted for the new set of images. A similar approach can be taken to fit a model for non-healthy subjects. LSE is a mathematical fitting approach with which the best-fitting curve to a set of points can be found by minimizing the sum of squared residuals. A residual is the difference between an observed value and the fitted value provided by a model. Thus, this effectively enables us to make a new training set using new images, or to extend an existing training set to include new images, based on the results obtained from an existing training set and using the image statistics of the new images.

Candidate subjects are tested in the same manner as for the "training" phase described above, and their reaction times analysed to correlate each individual to either the healthy or non-healthy category. This is illustrated schematically in FIG. 4. In this manner, it is possible to diagnose whether or not the individual is in the early stages of Alzheimer's disease.

In FIG. 4, each small circle represents patterns of reaction times (RTs) of one of the subjects. The shaded circles in the centre of each of the clusters 40, 42 are centroids of the cluster. $d_h$ is the distance between the patterns of reaction times for a candidate subject and the centroid of the cluster for healthy subjects, and $d_n$ is the corresponding distance from the centroid of non-healthy subjects.

After obtaining data from a new candidate subject, this data may be added to the applicable cluster 40, 42 of healthy or non-healthy subjects obtained from the "training" phase, to progressively grow the body of data against which future candidate subjects can be assessed. In the presently-preferred embodiments this is not done immediately after the candidate subject's test, but is left until the subject has been firmly diagnosed as having, or not having, dementia. Thus, in one embodiment we define a time-scale and track the candidate subject in that time-scale to see if he goes on to develop the disease or not; once this has been established we then add his patterns of reaction times to the relevant category to which he belongs.

Data Quantification and Correlation Technique

As discussed above, patterns of reaction times obtained from subjects are clustered into two categories of healthy and non-healthy subjects. For each subject there will be a vector of reaction times to a set of presented images, the vector having the same length as the number of images. Thus, in an overall test consisting of 500 images, we obtain a reaction time vector of length 500 for each subject. These vectors are used for the clustering.

For each image, statistical properties of the image are calculated and concatenated in a vector. The image statistics include entropy of the presented images, beta and gamma parameters of a Weibull distribution fitted to the edge histogram of the images, and Fourier slope and intercept of the images. So for each image there will be a vector of length 5 representing its statistical properties. By "a vector of length 5", this refers to the five image statistics mentioned in the previous sentence—i.e. (1) entropy, (2) gamma, (3) beta, (4) Fourier slope, and (5) Fourier intercept.

Figure 5:
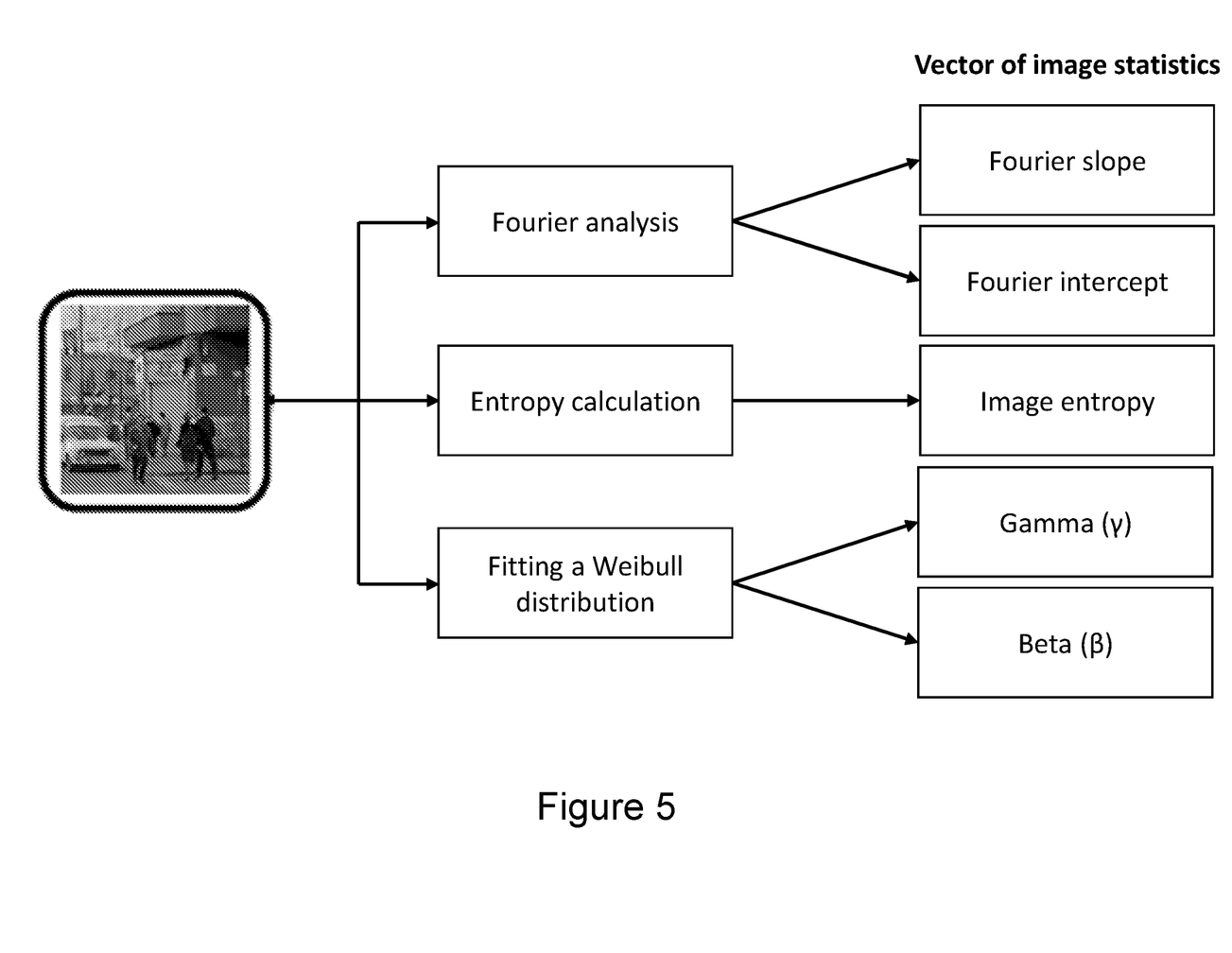
FIG. 5 illustrates an overview of a process of calculating a vector of image statistics.

FIG. 5 schematically illustrates, by way of an initial overview, the process of calculating the vector of image statistics for each image. For each image, Fourier analysis and entropy calculation are performed, and a Weibull distribution is fitted. From the Fourier analysis, the Fourier slope and Fourier intercept are obtained. From the entropy calculation, the image entropy is obtained. From the Weibull distribution, parameters gamma and beta are obtained.

Figure 6:
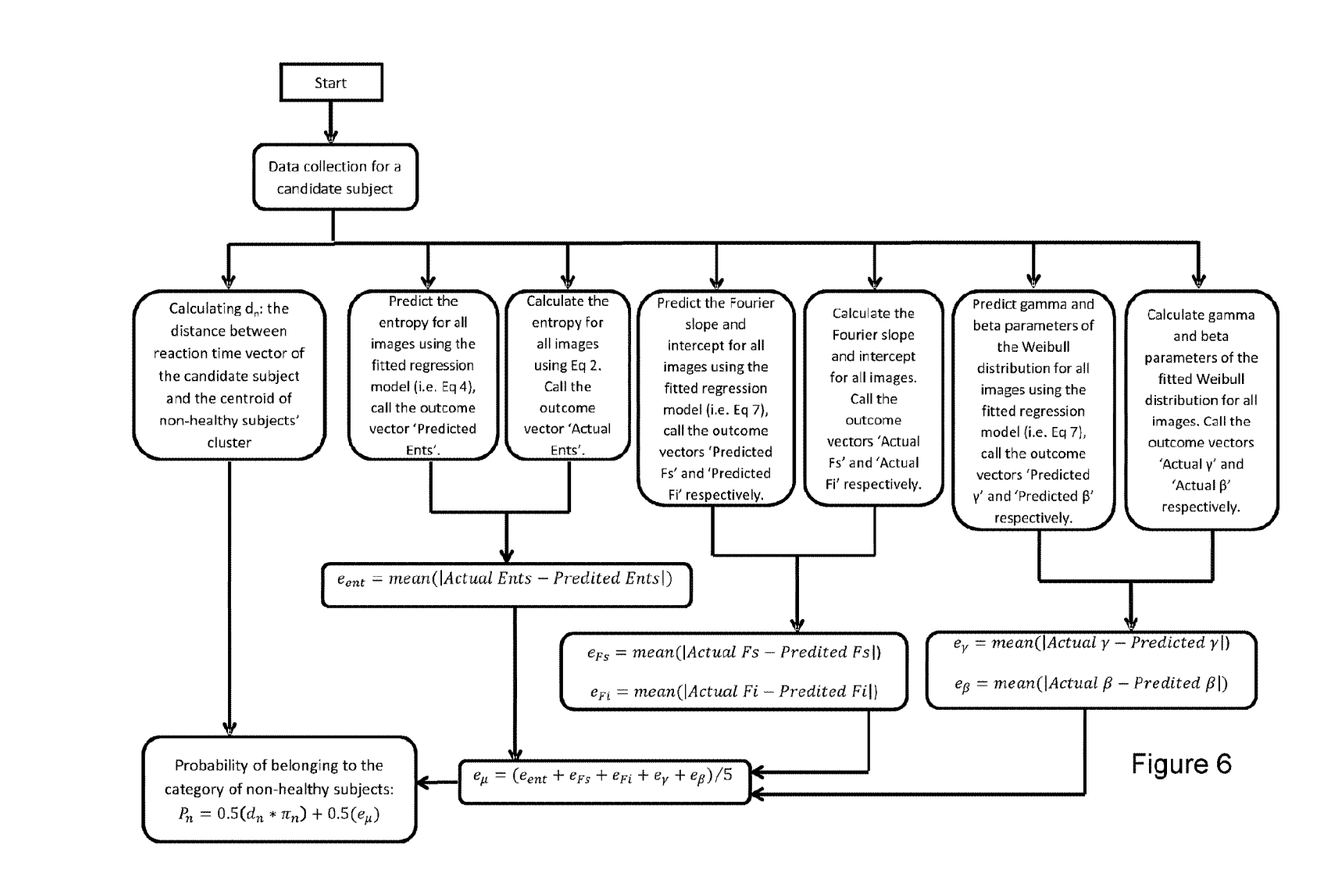
FIG. 6 illustrates in more detail the process of calculating a vector of image statistics.

FIG. 6 is a flow diagram illustrating the above five statistical properties in more detail. The properties involved are as follows:

Entropy

The entropy of an image is a measure of the amount of information it contains. The formulation for calculating the entropy is:

$$\text{Entropy} = -\Sigma(p_i \log(p_i)), \tag{1}$$

where i is a state and $p_i$ is the probability of that state.

To estimate the entropy of an input image I, we use the method proposed by Chandler and Field (2007). A group of 16 images are selected from the same category that image I belongs to (we call this group N). For image I and for each image in group N, $2^{14}$ non-overlapping patches of 8×8 pixels are extracted from top-left to the bottom-right of each image.

In this method the value for entropy is calculated using the following equation:

$$h(x) \cong C \sum_{m=1}^{M} \log_2 D_{N,m} + \log_2 \frac{A_q N}{q} + \frac{\rho}{\ln 2} \tag{2}$$

C is a $$\text{constant} = \frac{q}{M},$$

in which q=64 because of 8×8 patches, and M=$2^{14}$ total number of patches extracted from each image.

$D_{N,m}$ represents the minimum Euclidian distance between each patch of image I and those patches extracted from group N.

$$A_q = \frac{q\pi^{\frac{q}{2}}}{\text{gamma}\left(\frac{q}{2+1}\right)},$$

where gamma(x) is gamma function defined by $$\int_0^\infty t^x e^{-t} \frac{dt}{t}.$$

ρ is the Euler constant, approximately equal to 0.577.

Weibull Distribution

The edge histogram of a natural scene follows a Weibull distribution of the form in equation (3), which is a continuous probability distribution with two free parameters called beta (β) and gamma (γ).

$$f(x) = c \cdot \exp\left(\frac{x-\mu}{\beta}\right)\gamma, \quad (3)$$

where c is a normalization constant allowing f to be a probability distribution function. μ is the origin of the contrast distribution. β and γ respectively represent scale and shape parameters of the Weibull distribution.

The edge histogram for a given image is calculated by running an edge detector on the image and then counting the frequency of edges in different orientations. This gives us the histogram of edges in different orientations for the given image.

Fourier Analysis

Fourier statistics for an image can be derived by calculating the intercept and slope of a line fitted to the power spectrum of the image. The power spectrum for a given image can be derived by transferring the image to the Fourier space (e.g. using fast Fourier transform), and then plotting the proportion of the signal's power falling within given frequency bins.

Linear Regression

Considering the presented images and the response reaction time of healthy subjects to them, for each image, we define a mapping between healthy subjects' reaction time to the image, and the statistical properties of the image. The mapping is learnt by fitting a linear regression model between the reaction time of healthy subjects and each of the image statistics. As an example, for entropy, the linear regression model is the following:

$$En_i = RT_i * W_i + \varepsilon_i; \quad (4)$$

$\varepsilon_i$ is the error term.

$$En_i = [en_1, en_2, \ldots, en_l, \ldots, en_n], \quad (5)$$

where $En_i$ is the entropy of image i, and n is number of healthy subjects.

To fit the model, first all $en_i$ are initialized to the calculated entropy for image i, using equation (2).

$$RT_i = [rt_1, rt_2, \ldots, rt_l, \ldots, rt_n], \quad (6)$$

where $rt_l$ is the reaction time of subject l to image i.

Fitting the regression model means finding $W_i$ in equation (4) for each image.

Equations (4) and (5) can be generalized for an arbitrary image statistic as the following:

$$Ist_i = RT_i * W_i + \varepsilon_i; \quad (7)$$

$\varepsilon_i$ is the error term.

$$Ist_i = [ist_1, ist_2, \ldots, ist_l, \ldots, ist_n], \quad (8)$$

where $Ist_i$ is one of the mentioned image statistics calculated for image i, and n is number of healthy subjects.

For a candidate subject, we obtain the reaction times, then using the fitted regression model in equations 7 and 8, image statistics are estimated. The estimated image statistics are compared with the actual values of the image statistics and the error term (the difference between the actual and the predicted value) is used as a measure of accuracy. As the above formulae show, we do not do any dimensionality reduction; all the analysis and correlations between reaction times of a candidate subject and the cluster of healthy/non-healthy subjects are calculated in the original high dimensional space. FIG. 4 is only a simplification of this high-dimensional space mapped in 2-dimensional space for the sake of visualization.

The system uses the accuracy with which the subject presses YES or NO in response to the various images as a control measure to check whether the subject is paying attention to the task, or if he is merely responding in a random manner. If the latter is detected, his data will be deemed invalid, and he will either be removed from the training set or asked to redo the test.

An alternative, or additional, way of taking advantage of participants' response accuracy is to categorize participants into different groups based on their accuracy in the animal vs. non-animal task. Then, for a candidate subject, all comparisons may be done with the healthy and non-healthy subjects that fall in the same category as the candidate subject.

To enable the estimation of images statistics from the reaction times of a candidate subject, the estimated image statistics are compared against the actual image statistics. For a healthy candidate subject the estimation of image statistics is expected to be more accurate. This is another measure that we use to discriminate between healthy and non-healthy subjects.

Because we have five image statistics (as shown in FIGS. 5 and 6), we will have five error terms, $e_1, \ldots, e_5$. The average error is $e_\mu$; and we define the accuracy as $1-e_\mu$. For healthy subjects we expect to get higher accuracies.

For the candidate subject, we measure the correlation distance between their vector of reaction times and the centroid of the cluster for the reaction times of healthy subjects, and also non-healthy subjects. The distances are called $d_h$ and $d_n$ respectively (as marked in FIG. 4). For each cluster we also calculate the variance of the cluster; the inverse of the variance is called precision, $\pi_h, \pi_n$.

The probability of belonging to the category of non-healthy subjects is assigned to the candidate subject in the following way:

$$P_n = 0.5(d_n * \pi_n) + 0.5(e_\mu) \quad (9)$$

Network Architecture Diagram, Illustrating Data Flows Between Client Computers/Devices and Servers, Etc.

Figure 7:
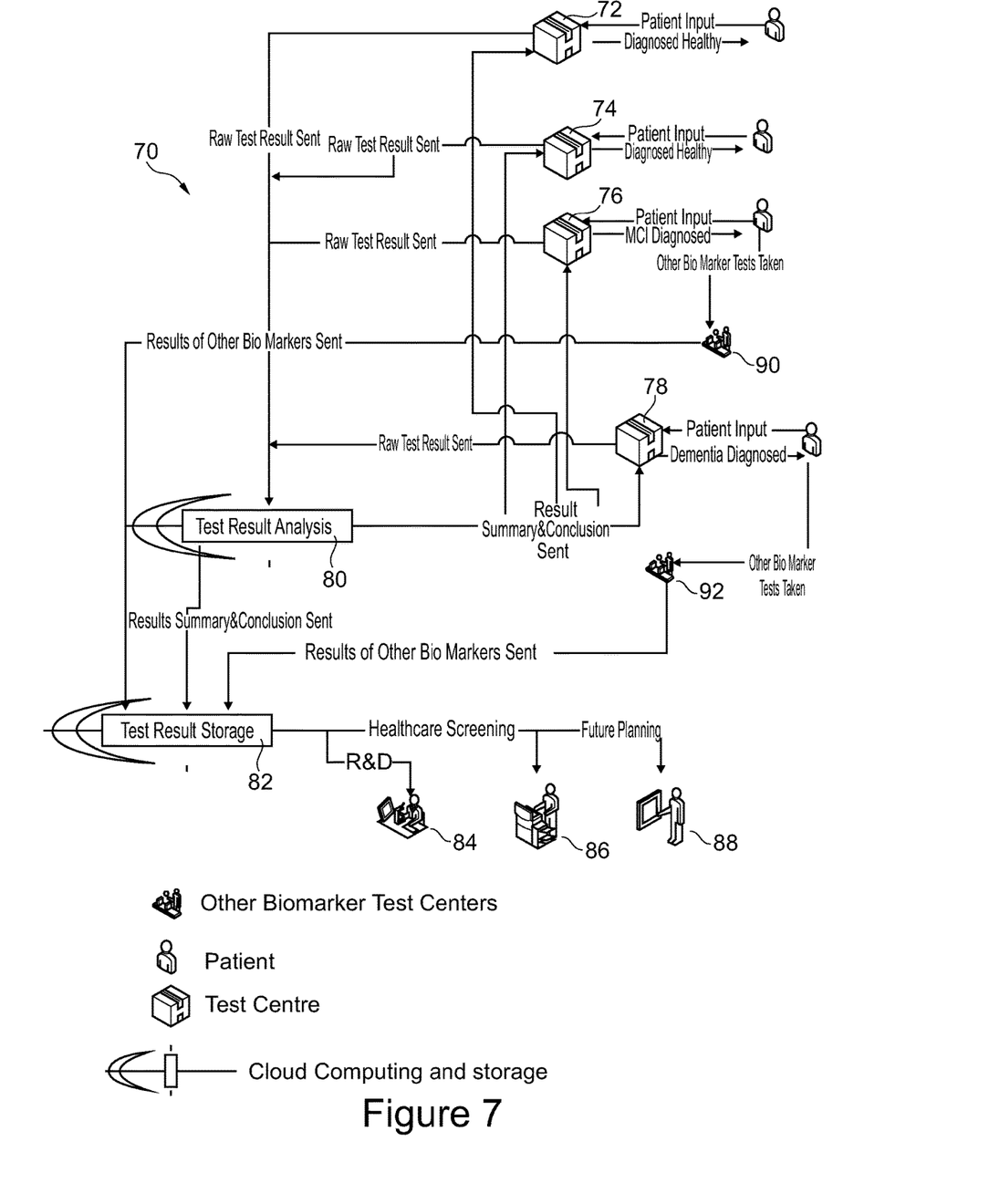
FIG. 7 is a network architecture diagram illustrating the flow of data between various test centres and network-based data analysis and data storage facilities.

FIG. 7 is a network architecture diagram illustrating the flow of data between various test centres and network-based data analysis and data storage facilities, when carrying out tests on individual candidate subjects. Computers in test centres 72, 74, 76 and 78 are used to perform the image recognition test as described above. The test centres can be in different locations (e.g. different rooms in the same building, different buildings, different cities or different countries). The network 70 may be a wide area network such as the Internet, as those skilled in the art will appreciate.

The test results are sent, via the network 70, to a remote server 80 configured to analyse the results and to send the results (summary and conclusions) back to the test centres 72, 74, 76, 78.

In the example illustrated, the results returned to test centres 72 and 74 diagnose the patient as being healthy. On the other hand, the results returned to test centre 76 diagnose the patient has having mild cognitive impairment (MCI). In view of this, other biomarker tests are taken from the patient and sent to a biomarker test centre 90 for further diagnosis. Likewise, the results returned to test centre 78 diagnose the patient has having dementia. In view of this, other biomarker tests are taken from the patient and sent to a biomarker test centre 92 for further diagnosis.

The results (summary and conclusions) are also sent from the analysis server 80 to remote storage device 82 (which may be the same physical device as server 80, or different) for storage. The results from the other biomarker tests are also sent from test centres 90 and 92 to storage device 82 for storage.

Within the storage device 82, the data obtained from these tests can be added to the clusters of data for healthy and non-healthy patients obtained in the initial data collection phase (e.g. clusters 40 and 42 shown in FIG. 4), to grow the body of data against which future candidate subjects can be assessed.

Data from storage device 82 may also be supplied (subject to all necessary data protection provisions) for research and development purposes (84), healthcare screening purposes (86) and future planning purposes (88).

Multiple instances of results obtained from a given individual over time may be stored. Furthermore, trend analysis may be performed using those results, to detect the onset of dementia in respect of that individual.

As those skilled in the art will appreciate, the processes described herein may be implemented by a computer program or a set of instruction code capable of being executed by a microprocessor (e.g. within a computer in test centres 72, 74, 76 and 78, or in servers 80 or 82). The computer program or set of instruction code may be supplied on a computer-readable medium or data carrier such as a CD-ROM, DVD or solid state memory device. Alternatively, it may be downloadable as a digital signal from a connected computer, either directly or over a local area network or a wide area network such as the Internet. As a further alternative, the computer program or set of instruction code may be hard-coded in the microprocessor (or memory associated therewith) that is to execute it.

OTHER POSSIBLE MODIFICATIONS AND ALTERNATIVES

Detailed embodiments have been described above. As those skilled in the art will appreciate, a number of additional modifications and alternatives can be made to the above embodiments whilst still benefiting from the inventions embodied therein.

For example, in the above embodiments, the categorisation-based image processing task is whether or not each test image contains an animal. However, alternative embodiments may use other image processing criteria, such as, for example, whether or not each test image contains a man-made object.

In the above embodiments the system is configured to display each test image for a duration of 12.5 ms, followed by the blank screen for a duration of 12.5±0.6 ms, followed by the noisy mask for a duration of 100 ms. However, in alternative embodiments different lengths of time for these display operations may be used.

The paradigm of masking that is described above is called backward masking, where the mask appears after the stimulus offset. However, the invention is not limited to this type of masking; other masking paradigms (e.g. object substitution masking) can be used instead. Furthermore, the nature of the mask stimulus is not restricted only to the 1/f noise mask as described above; other mask images (e.g. scrambled images) can also be used.

In the above embodiments the statistical processes performed on the images were Fourier analysis (to find the Fourier slope and the Fourier intercept), image entropy, and the fitting of a Weibull distribution (to find the Weibull parameters gamma and beta). However, in alternative embodiments other image statistics may be used.

In the above embodiments the mental health disorder being assessed is dementia, and more particularly Alzheimer's disease (AD). However, in alternative embodiments, by collecting data from subjects with other brain disorders (e.g. other types of dementia), our cognitive test can be extended for the diagnosis of brain disorders other than AD.

Finally, collecting enough data for several brain disorders allows our novel cognitive test to be used as a general framework for testing people's brain healthiness.

Various other modifications and alternatives will be apparent to those skilled in the art and will not be described in further detail here.

SUMMARY

Various features and advantages of the above-described embodiments can be summarised as follows:
- We propose a computerized task for early diagnosis of Alzheimer's disease (AD).
- We target brain functionalities that are affected at the initial stages of the disease development, specifically before the start of memory symptoms.
- Brain functionalities includes subject's ability and speed in visual processing, and classification.
- The task also engages motor cortex.
- The task is a rapid animal vs. non-animal categorization task.
- We measure subject's response reaction times (RT) to a set of natural images shown in the categorization task.
- Stimuli are presented for a very short duration (12.5 ms), followed by a 12.5±0.6 ms blank screen, followed by a mask (100 ms).
- Subjects should fixate to the fixation point during the task; and they are asked to have 50 cm distance from the screen.
- Based on the patterns of measured RTs a model will be developed for each category of subjects (i.e. healthy vs. AD)
- We diagnose those with AD by comparing their patterns of reaction times to the models developed for healthy and AD subjects.
- For each subject we assign a probability of the category he/she belongs to based on the correlation of his/her pattern of reaction times to the fitted model of reaction times for healthy or non-healthy subjects.

Subjects' response reaction times are correlated with statistical properties of natural images presented.

The image statistics include entropy of the presented stimuli, beta and gamma parameters of a Weibull distribution fitted to the edge histogram of the input stimuli, Fourier slope and intercept of the stimuli.

The entropy of an image is a measure of the amount of information it contains.

The edge histogram of a natural scene follows the Weibull distribution, which is a continuous probability distribution with two free parameters called beta and gamma.

Fourier statistics for an image can be derived by calculating the intercept and slope of a line fitted to the power spectrum of the image.

We select those image statistics that increase the discriminability between healthy and non-healthy subjects.

The idea can be generalized to other types of dementia by developing a model for each type of the disease.

The proposed method is extendible for diagnosis of other types of brain disorders and mental health problems.

REFERENCES

Armstrong, R. (2012). The visual cortex in Alzheimer disease: laminar distribution of the pathological changes in visual areas V1 and V2. In Visual Cortex, J. Harris, and J. Scott, eds. (Hauppage, N.Y. (US): Nova science), pp. 99-128.

Brewer, A. A., and Barton, B (2012). Visual cortex in aging and Alzheimer's disease: Changes in visual field maps and population receptive fields. Front. Psychol.-1.

Gordon, B., and Carson, K. (1990). The basis for choice reaction time slowing in Alzheimer's disease. Brain Cogn. 13, 148-166.

Chandler D M, Field D J (2007) Estimates of the information content and dimensionality of natural scenes from proximity distributions. JOSA 24: 922-941.

Jahanshahi, M., Brown, R. G., and Marsden, D. (1992). Simple and Choice Reaction Time and the Use of Advance Information for Motor Preparation in Parkinson's Disease. Brain 115, 539-564.

Knopman, D., and Nissen, M. J. (1991). Procedural learning is impaired in Huntington's disease: Evidence from the serial reaction time task. Neuropsychologia 29, 245-254.

Mentis, M. J., Horwitz, B., Grady, C. L., Alexander, G. E., VanMeter, J. W., Maisog, J. M., Pietrini, P., Schapiro, M. B., and Rapoport, S. I. (1996). Visual cortical dysfunction in Alzheimer's disease evaluated with a temporally graded "stress test" during PET. Am. J. Psychiatry 153, 32-40.

Mirzaei, A., Khaligh-Razavi, S.-M., Ghodrati, M., Zabbah, S., and Ebrahimpour, R. (2013). Predicting the Human Reaction Time Based On Natural Image Statistics in a Rapid Categorization Task. Vision Res.

Rinehart, N. J., Bradshaw, J. L., Brereton, A. V., and Tonge, B. J. (2001). Movement Preparation in High-Functioning Autism and Asperger Disorder: A Serial Choice Reaction Time Task Involving Motor Reprogramming. J. Autism Dev. Disord. 31, 79-88.

The invention claimed is:

1. A system for assessing a mental health disorder in a human subject, the system comprising:
    a display configured to display a series of natural test images to the subject;
    an input by which the subject can input a response, following the display of each test image, as to whether or not the test image satisfies a predetermined categorization criterion;
    control processor configured to control the display of the test images by the display, to measure the duration of time from when each test image is initially displayed to when the corresponding response is input by the subject, and to generate a set of response data including the response times with respect to each of the test images; and
    a data processor configured to process the set of response data and to compare the processed response data with reference data to assess whether or not the subject has, or is likely to develop, the mental health disorder,
    wherein the control processor is configured to cause the display to display each test image for a duration of the order of 10 ms, followed by a blank screen for a duration of the order of 10 ms, followed by a noisy mask for a duration of the order of 100 ms or longer.

2. The system of claim 1, wherein the control processor is configured to cause the display to display each test image for 12.5 ms.

3. The system of claim 1, wherein the control processor is configured to cause the display to display the blank screen for a variable length of time after each test image.

4. The system of claim 3, wherein the control processor is configured to cause the display to display the blank screen for a variable length of time of between 11.9 ms and 13.1 ms after each test image.

5. The system of claim 1, wherein the control processor is configured to cause the display to display 1/f or 'pink' noise as the noisy mask.

6. The system of claim 1, wherein the predetermined categorization criterion is whether the image includes an animal.

7. The system of claim 1, wherein the control processor is configured to cause the display to display a total of approximately 500 test images to the subject during the course of a test.

8. The system of claim 1, wherein the data processor is configured to compare the processed response data with reference data obtained by previously testing subjects without the mental health disorder and subjects with the mental health disorder.

9. The system of claim 1, wherein the data processor is configured to compare the processed response data with predicted or estimated reference data obtained by performing statistical analysis on one or more of the test images used.

10. The system claim 9, wherein the statistical analysis is used to obtain a measure of the complexity of the said one or more test images.

11. The system of 10, wherein the statistical analysis takes into account one or more of the entropy, the Weibull distribution and Fourier analysis of the said one or more test images.

12. The system of claim 1, wherein the data processor is configured to process the set of response data so as to produce a vector of reaction times with respect to the subject, and to compare said vector with clusters of such vectors representative of healthy and non-healthy subjects.

13. The system of claim 1, further comprising a data storage device in communication with the data processor, for storing the results produced.

14. The system of claim 13, wherein the data storage device is configured to store multiple instances of results obtained over time from a given subject.

15. The system of claim 14, further comprising a processor configured to perform trend analysis on the results obtained from the given subject over time.

16. The system of claim 1, wherein the data processor is configured to add to the reference data the processed response data obtained with respect to the subject, once the mental health of the subject has been diagnosed.

17. The system of claim 1, wherein the mental health disorder is dementia or Alzheimer's disease.

18. A computerized method for assessing a mental health disorder in a human subject, the method comprising:
- displaying a series of natural test images to the subject;
- receiving response input from the subject, following the display of each test image, as to whether or not the test image satisfies a predetermined categorization criterion;
- measuring the duration of time from when each test image is initially displayed to when the corresponding response input is received from the subject;
- generating a set of response data including the response times with respect to each of the test images; and
- processing the set of response data and comparing the processed response data with reference data to assess whether or not the subject has, or is likely to develop, the mental health disorder;
- wherein the display of each test image is for a duration of the order of 10 ms, followed by a blank screen for a duration of the order of 10 ms, followed by a noisy mask for a duration of the order of 100 ms or longer.

19. A non-transitory computer readable medium storing a program which, when executed by a processor, causes the processor to implement a method for assessing a mental health disorder in a human subject, the method comprising:
- displaying a series of natural test images to the subject;
- receiving response input from the subject, following the display of each test image, as to whether or not the test image satisfies a predetermined categorization criterion;
- measuring the duration of time from when each test image is initially displayed to when the corresponding response input is received from the subject;
- generating a set of response data including the response times with respect to each of the test images; and
- processing the set of response data and comparing the processed response data with reference data to assess whether or not the subject has, or is likely to develop, the mental health disorder;
- wherein the display of each test image is for a duration of the order of 10 ms, followed by a blank screen for a duration of the order of 10 ms, followed by a noisy mask for a duration of the order of 100 ms or longer.

* * * * *